United States Patent [19]
Rappold

[11] Patent Number: 5,944,529
[45] Date of Patent: Aug. 31, 1999

[54] TWO-COMPONENT DENTAL POST SYSTEM

[75] Inventor: Allan P. Rappold, Kenner, La.

[73] Assignees: Board of Supervisors of Louisiana State University; Agricultural and Mechanical College

[21] Appl. No.: 09/177,684

[22] Filed: Oct. 22, 1998

[51] Int. Cl.[6] .................................................. A61C 5/08
[52] U.S. Cl. ............................................................. 433/221
[58] Field of Search .................................. 433/173, 174, 433/220, 221, 224, 225

[56] References Cited

U.S. PATENT DOCUMENTS

| | | | |
|---|---|---|---|
| 3,524,255 | 8/1970 | Kurer ........................................ | 433/221 |
| 4,348,183 | 9/1982 | Weissman ................................ | 433/221 |
| 4,490,116 | 12/1984 | Deutsch et al. . | |
| 4,515,565 | 5/1985 | Winter-Moore et al. . | |
| 4,846,685 | 7/1989 | Martin . | |
| 5,073,112 | 12/1991 | Weil . | |
| 5,236,361 | 8/1993 | Mays . | |
| 5,263,996 | 11/1993 | Filhol . | |
| 5,284,443 | 2/1994 | Weil . | |
| 5,409,377 | 4/1995 | Mays ....................................... | 433/220 |

OTHER PUBLICATIONS

"CYTCO®: System of Parallel–Tapered Root Posts, Titantium (USA/ASTM Grade 5)," Instruction Booklet, Caulk/Dentsply, The L.D. Caulk Division (1990).

"Flexi–Cast™: Instruction Booklet," Essential Dental Systems, Inc. (1990).

"ParaPostXT™: Threaded Endodontic Post System," Instruction Booklet, Coltene/Whaledent, Inc. (1993).

"Rock Solid Restorative Systems, Flexi–Post®, Flexi–Flange®, TI–Core®, and Flex–Flow®," Undated Advertisement, Essential Dental Systems.

"Three Post Systems from Brasseler," 1998 Advertisement, Brasseler USA®.

*Primary Examiner*—Nicholas D. Lucchesi
*Attorney, Agent, or Firm*—Bonnie J. Davis; John H. Runnels

[57] ABSTRACT

A two-component, dental post system uses two components to both improve the fit of the post to the tooth and increase retention of the post. This post system has a threaded inner post that is screwed into the apical portion of the canal and an outer sleeve that is screwed into the coronal portion of the canal with threads whose handedness is opposite to those on the inner post. When the two components are bonded together at the top by dental cement or resin, the opposing threads on the two components resist rotational forces in both directions and thus increase retention. In addition, this dental post system can be removed if necessary for further treatment of the tooth by shearing or cutting the cemented top portion of both components and then unscrewing the components one at a time.

16 Claims, 8 Drawing Sheets

TWO-COMPONENT DENTAL POST SYSTEM

This invention pertains to a two-component dental post system, each component having opposing threads to increase retention in the tooth by resisting rotational forces from different directions.

When a tooth is weakened by decay or fracture, the tooth is often treated by performing a root canal, which involves cleaning, shaping, and ultimately filling the space inside the tooth where the nerve and blood vessels used to reside with an inert material, usually gutta percha. After such treatment, the tooth would be vulnerable to additional decay without protection. Protection for the tooth is usually achieved by inserting a dental post into the cleaned space, and then making a core around the top of the post to support a crown or other protective top. This treatment is referred to as either "foundational build-up" or "post and core build-up." These foundational "build-ups" of root-canal treated teeth are important in both anterior and posterior teeth. Each tooth that requires such build-up treatment is unique in shape. Thus finding a suitable post and core build-up system that will fit and be retained in the various sizes of teeth is difficult.

In deciding what post and core system to use, the primary consideration is retention. The size, including both width and length, and shape of the post influence the retention time. A wider post is stronger and lends greater support to the core and protective top. However, a wide post requires that a wider canal be drilled in the tooth and thus can weaken the tooth even further. A narrow post requires a smaller canal and leaves more of the original tooth, but is not as strong. In view of this dilemma, many prefabricated posts have a wider diameter for the proximal portion that extends into the coronal portion of the tooth than for the distal portion that extends into the apical portion of the tooth. Prefabricated posts also come in various lengths to adjust to the length of the drilled canal. A secondary consideration in deciding which post system to use is the ease of removing the post should the tooth need additional treatment.

There are several forces that work against the retention of the dental post and core build-up in the tooth. These forces can be characterized as either axial or rotational. Axial forces tend to pull the post out of the tooth. Rotational forces tend to twist the post in the tooth and thus loosen the bond between the post and the tooth. Rotational forces are a major cause of post failure and shortened retention time, especially in prefabricated post systems with cylindrical posts.

Retention of the post in the tooth is improved by proper fit of the post in the tooth. Most root canals are drilled wider in the coronal (top) portion of the tooth and narrower at the apical (tooth root) portion to achieve a balance between strength and retention. However, this two-diameter canal increases the difficulty of fitting a one-piece post and of maximizing tooth-to-post contact.

Current dental post systems are retained in the tooth by either "passive" or "active" methods, or by a combination of the two. In "passively" retained systems, the post system relies totally upon the use of dental cement to adhere the post to the remaining tooth structure. An "active" system, on the other hand, uses threads on the post that mechanically engage the tooth inside the root canal. Active systems have been shown to be more retentive than passive systems, especially if the post is both threaded and cemented in place. A major problem with prior "active" systems is the lateral force placed upon the sides of the tooth during insertion. The inflexible design of some active systems can cause significant tooth fracture. Tapering the post entering the tooth canal and making the distal portion of the post flexible by using a split shank are techniques that have been used to reduce this stress.

The traditional post system is a custom cast system in which a cast or mold is made of the drilled canal, and a post and core (top) are then cast from the mold. This technology is still considered one of the best, because the entire usable length of the canal is used for retention of the post unit. This system resists rotational forces because the post does not have a circular cross section and thus does not tend to rotate. However, the cast system has a number of disadvantages. A primary disadvantage is the requirement of at least two visits to the dentist-first to make the mold and then to place the cast post in the tooth. A second disadvantage is that retention is based upon "passive" principles only and thus depends entirely upon the strength of the dental cement. Finally, should the tooth need retreatment, a well-constructed cast post and core is almost impossible to remove from the canal because the post cannot be rotated without breaking the remaining tooth structure.

The post systems used by most dentists today are commercially available, prefabricated systems, e.g., FLEXI-POST®, FLEXI-CAST™, FLEXI-FLANGE®, TI-CORE®, and FLEXI-FLOW® offered by Essential Dental Systems, S. Hackenbeck, N.J.; OPTIPOST™, CERAPOSTT™, and Vlock™ offered by Brasseler USA, Savannah, Ga.; ParaPostXT™ offered by Coltene/Whaledent Inc., Mahweh, N.J.; and CYTCO® offered by The L.D. Caulk Division, Milford, Del. See "CYTCO®: System of Parallel-Tapered Root Posts, Titantium (USA/ASTM Grade 5)," Instruction Booklet, Caulk/Dentsply, The L. D. Caulk Division (1990); "Flexi-Cast™: Instruction Booklet," Essential Dental Systems, Inc. (1990); "ParaPostXT™: Threaded Endodontic Post System," Instruction Booklet, Coltene/Whaledent, Inc. (1993); "The Rock Solid Restorative Systems, FLEXI-POST®, FLEXI-FLANGE®, TI-CORE®, and FLEXI-FLOW®," Undated Advertisement, Essential Dental Systems; and "Three Post Systems from Brasseler," 1998 Advertisement, Brasseler USA®.

These prefabricated systems are simple to use, economical, and require only a single visit to the dentist. The retention time of these systems has been shown to be good. The posts have circular cross-sections, and thus the major factor in failure has been rotational stress around the central axis of the post. Prefabricated systems are made in various diameters to match the standard dental drills used to prepare the canal. Although in most prefabricated systems the post is threaded into the tooth, these threads are oriented in a single direction and therefore offer resistance to rotation in one direction but not the other. A wider coronal canal is often accommodated in a unitary post with a top portion wider than the distal portion. The degree of fit to the drilled canal depends on the number of available options for post lengths and diameters. One of these prefabricated systems, the FLEXI-CAST™, is a two component system consisting of a shaft and an outer sleeve; however, only the shaft has threads. An advantage of these prefabricated systems over post and core casts is that retrieval of the post is less likely to result in damage to the tooth.

U.S. Pat. No. 5,284,443 describes a method for securing a single-piece dental post by placing a curable compound into the tooth and creating a lining inside the tooth. This lining is then drilled, and the post inserted and cemented to the lining.

U.S. Pat. No. 5,263,996 describes a single-piece tapered dental "pin" with external threads. The pin is pushed into the canal of the tooth after filling the canal with dental cement. The purpose of the threads, which engage the tooth only at the top of the canal, is to hold the pin stationary while the dental cement cures.

U.S. Pat. No. 5,236,361 describes a single-piece dental post in which the distal portion has an elongated slot, creating a split shank that reduces the lateral force exerted on the tooth as the post is pushed into the apical canal. The post is secured to the tooth with dental cement.

U.S. Pat. No. 5,073,112 describes a single-piece dental post with threads running in a single direction. After filling the canal with a light curable composite, a mandrel (a model of the post) is inserted in the bore until the cement cures. The mandrel is then removed, leaving a canal in the composite that matches the dental post. The post is then threaded into the canal and cemented in place.

U.S. Pat. No. 4,846,685 describes a single-piece, perforated dental post which uses perforations to increase the surface area available for bonding to the core material. Prior to insertion, the perforations and the tooth canal are filled with dental cement. The excess cement and hydrostatic forces that are created during insertion are vented through the perforations.

U.S. Pat. No. 4,515,565 describes a one-piece dental post with an enlarged adjustable head called a bush. A stainless steel post is threaded into the apical canal to a desired depth. The bush is moved on the post with threads internal to the bush until seated in the coronal cavity. The bush acts as a lock nut on the post. The bush does not have external threads and does not engage the tooth itself. The bush is secured to the tooth through the use of dental cement.

U.S. Pat. No. 4,490,116 describes a wrench and a one-piece dental post with a split shank. The dental post is tapped and threaded into the tooth and anchored by dental cement.

I have discovered a dental post system that uses two components to both improve the fit of the post to the tooth and increase retention of the post. This post system has a threaded inner post that is screwed into the narrow apical portion of the canal and an outer sleeve that is screwed into the wider coronal portion of the canal with threads whose handedness is opposite to those on the inner post. When the two components are bonded together at the top by dental cement or resin, the opposing threads on the two components resist rotational forces in both directions and thus increase retention. In addition, this dental post system can be removed if necessary for further treatment of the tooth by first shearing or cutting the cemented top portion of both components, and then unscrewing the components one at a time.

The purpose of this invention is to provide a dental post with increased retention time in an endodontically treated tooth. The tooth is prepared by drilling a canal of a predetermined length with drills of two diameters—a narrow diameter for the apical portion of the canal and a wider diameter for the coronal portion of the canal. The post system comprises two parts, an inner post and an outer sleeve. Both components are made of noncorrosive material and are preferably made in industry standard diameters and lengths to fit standard drill and tooth sizes. In a two-component system, the inner post and outer sleeve can be mixed and matched depending upon the size of the tooth, thus improving the fit to the tooth. The inner post has external threads and tapered legs with one or more, preferably two, elongated slots. The inner post is threaded into the apical portion of the canal, engaging the dentin of the tooth. The inner post can be threaded with a tool similar to a wrench whose socket size fits the outer shape of the top of the inner post. The inner post may optionally also be cemented into the apical portion of the canal to increase retention. The tapered, split shank legs of the inner post flex during insertion to relieve forces that might otherwise tend to fracture the tooth. The inner post is threaded into the tooth until its positive seat engages the coronal ledge, i.e., the ledge created by the different diameters of the apical and coronal canals.

The outer sleeve, which has a smooth inner surface and outer threads, slides over the inner post while being threaded into the dentin of the coronal portion of the canal until the outer sleeve reaches the coronal ledge. The inner post and outer sleeve are then bonded together at the top portion through perforations in both components that allow dental cement or resin to flow freely into and around the two components in the top portion that is above the tooth surface. Once the two components are bonded together, the opposing threads of the components combine to resist rotational forces in either direction that might otherwise tend to loosen the post. If a need arises for the tooth to be retreated, the post system may be removed. First, the bonded top portions of the inner post and outer sleeve must be removed by sectioning, thus breaking the cemented bond between the two components. Then outer sleeve can be rotated independently, and screwed out of the tooth. Finally, the inner post can be screwed out of the tooth.

This new post system for endodontically treated teeth provides support and improved retention in the tooth stub for prosthetic devices and crowns. One embodiment of the invention is depicted in the accompanying drawings.

Figure 1:
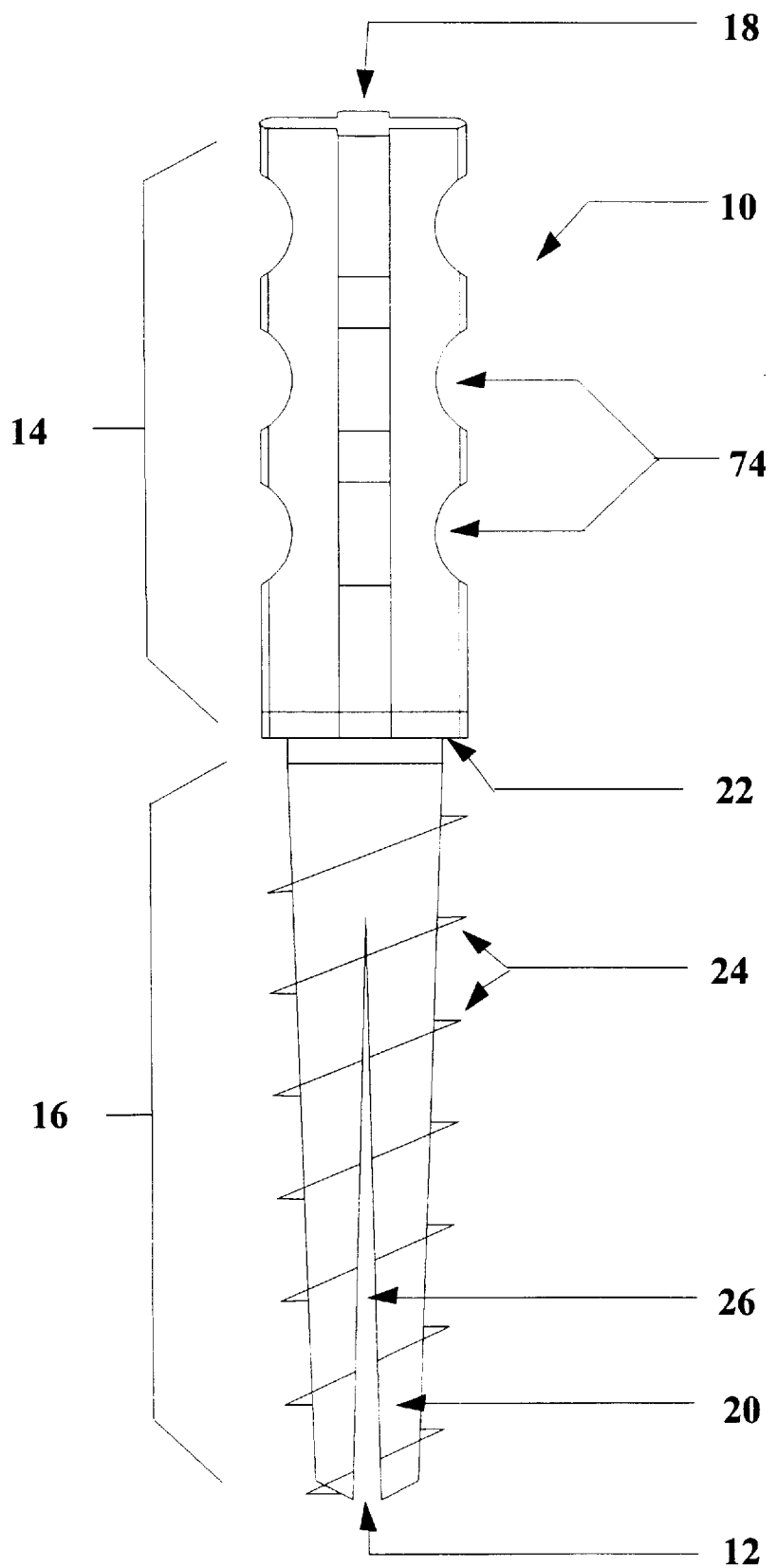
FIG. 1 illustrates a side view of the inner post component of the dental post.

FIG. 1 illustrates the inner post 10. The inner post 10 has a distal end 12 and a proximal end 18 The distal portion 16 has a circular cross-section with two or four tapered legs 20 which are separated by one or more elongated slots 26. The purpose of the slot(s) 26 and tapered legs 20 is to allow the legs to flex when inserted in the tooth, thereby reducing the stress on the tooth and decreasing the possibility of tooth fracture. The elongated slot(s) 26 also allows for venting of hydrostatic forces and debris as the inner post is screwed into the tooth. The distal portion 16 has external threads 24, shown in a clockwise direction in this embodiment of the invention. These threads 24 engage the dentin of the tooth when inserted and secure the post to the tooth by "active" means. Between the distal portion 16 and the proximal portion 14 is a positive seat 22. The positive seat 22 engages a ledge in the coronal cavity formed by two different diameter drills, and prevents over-insertion of the post. The proximal portion 14 is a crossed-bar shape in cross-section with a width either equal to or slightly larger that the diameter of the distal portion 16. The length of the proximal portion 14 can be shaped or shortened by sectioning or drilling the top portion down. The side bars have perforations 74 to increase the surface area of the proximal portion 14 and thus increase the strength of the bond between the proximal portion 14 of the inner post 10 and the outer sleeve 50 (FIG. 2) when the two are cemented together. The surface of the proximal portion 14 may also be "sandblasted" or otherwise roughened to increase the surface area for bonding.

Figure 2:
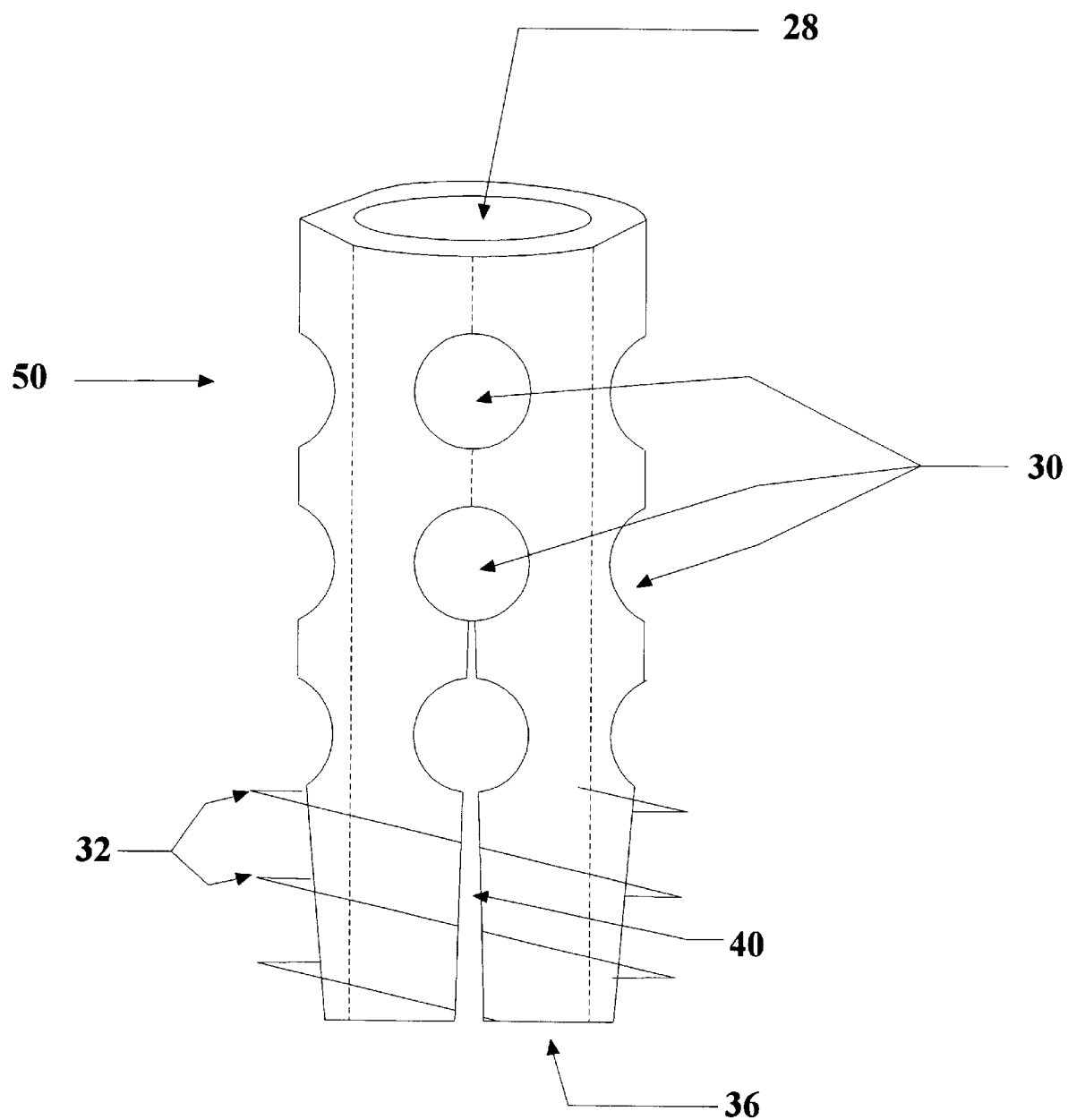
FIG. 2 illustrates a side view of the outer sleeve component of the dental post.

FIG. 2 illustrates the outer sleeve 50. The outer sleeve 50 has one or more slots 40 which reduce stress during insertion into the coronal portion of the canal by allowing the sleeve to flex. The outer sleeve 50 has a cylindrical channel 28 which slides over the proximal portion 14 of the inner post 10 during insertion of the outer sleeve 50. The diameter of the cylindrical channel 28 of the outer sleeve 50 is matched to the outer cross-sectional width of the proximal portion 14 of the inner post 10. The surface of the channel 28 can also be "sandblasted" or otherwise roughened to increase the surface area for bonding between the inner post 10 and the outer sleeve 50. The outer sleeve 50 is flattened on the distal end 36 to provide a positive stop against the coronal ledge during insertion. The outer sleeve 50 has external threads 32 which are in the opposite direction of the threads 24 on the inner post 10. The outer sleeve 50 has multiple holes 30. These holes 30 and the perforations 74 on the proximal portion 14 of the inner post 10 enable dental cement or resin both to flow between the outer sleeve 50 and the inner post 10 and to provide a uniform and continuous build up of the composite core cement.

Figure 3:
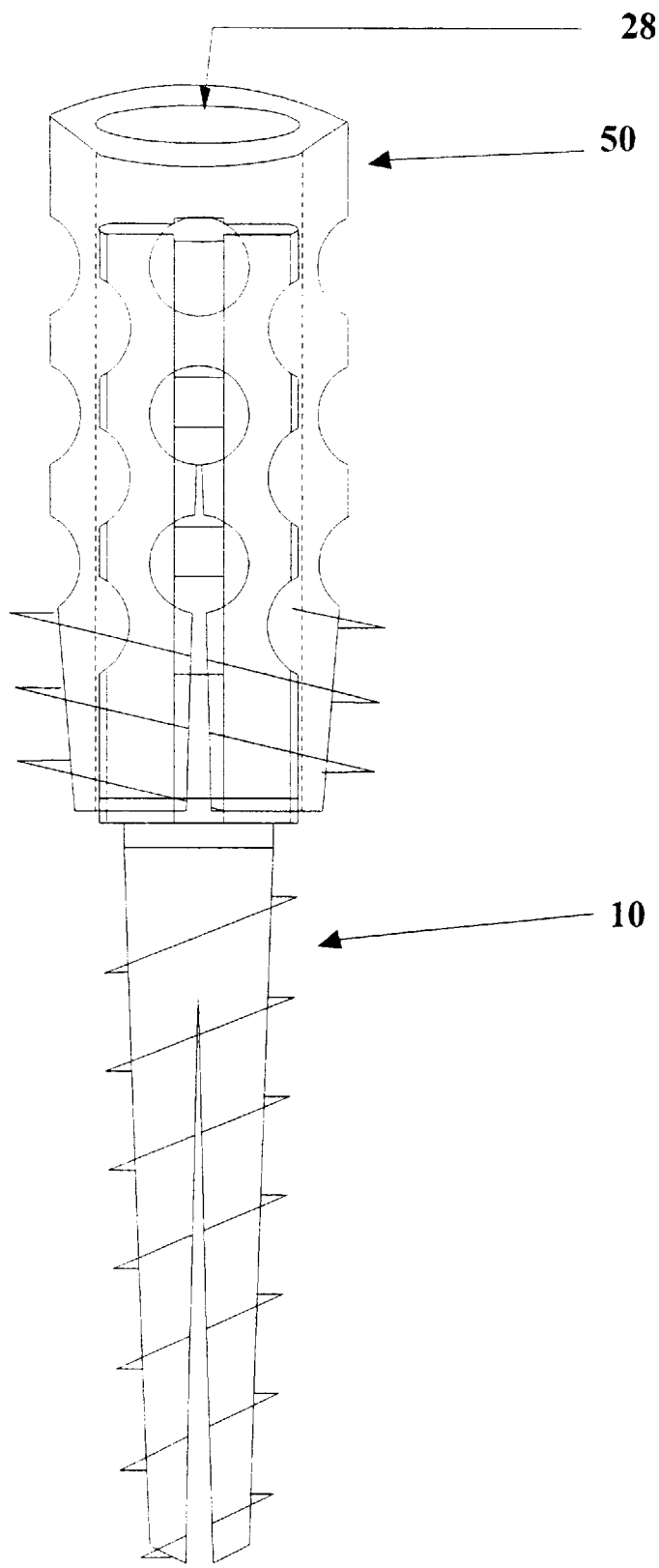
FIG. 3 illustrates the joining of the inner post and outer sleeve.

As shown in FIG. 3, the outer sleeve 50 slides over the inner post 10. The inner post correspondingly slides into channel 28 of the outer sleeve 10.

Figure 4:
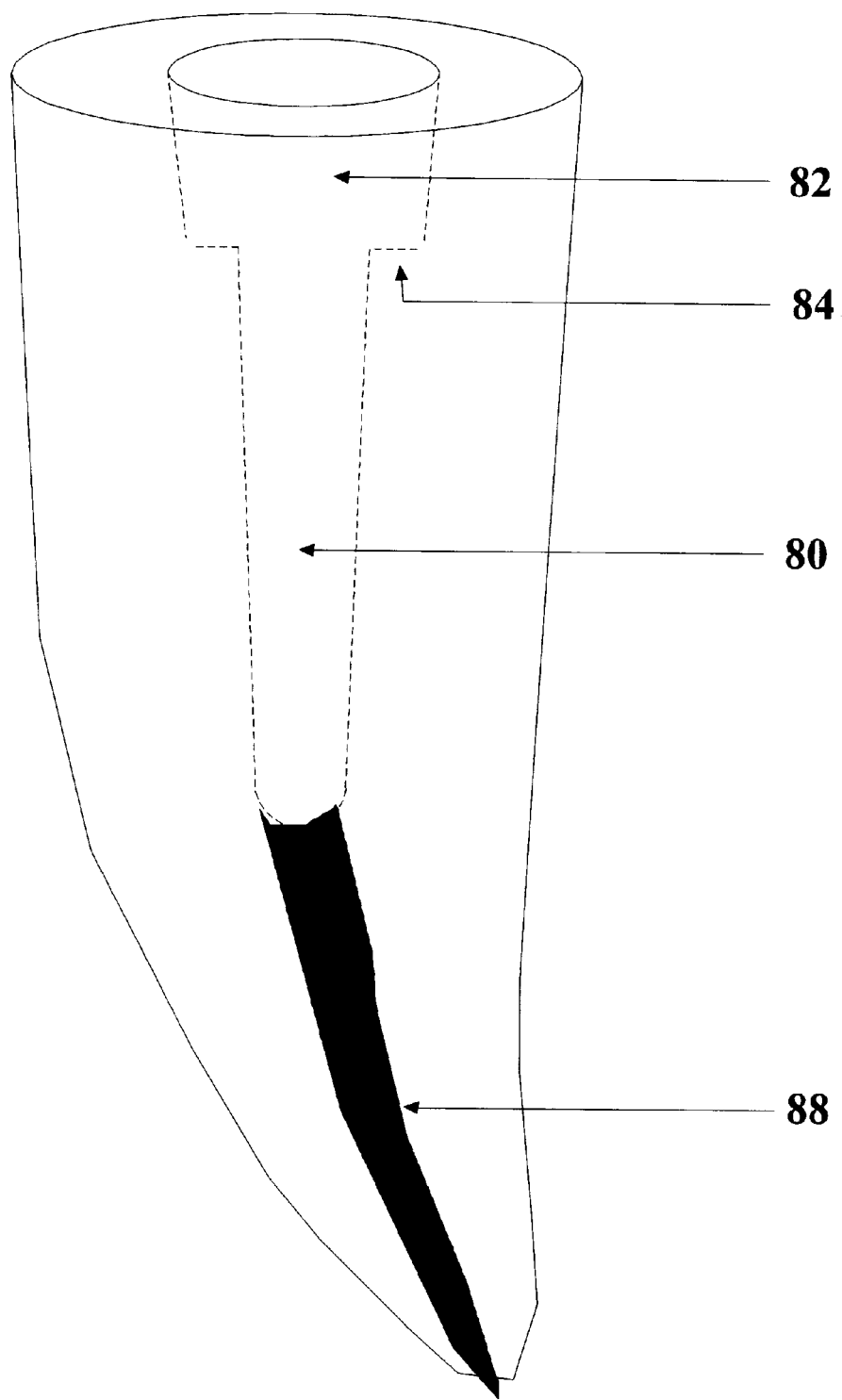
FIG. 4 illustrates a tooth after a root canal, prepared with two diameters for the post system of the present invention.

FIG. 4 illustrates the preparation of a tooth partially filled with gutta percha 88 after conventional root canal work. The narrower apical canal 80 maximizes the amount of tooth remaining to support the post. The wider coronal canal 82 provides more support for the core and protective top. The coronal ledge 84 is formed at the juncture of the wider coronal canal 82 and the narrower apical canal 80. The diameter of both the apical canal 80 and the coronal canal 82 is drilled to match one of the various diameters available for the distal portion 16 of the inner post 10 and the outer sleeve 50, respectively.

Figure 5:
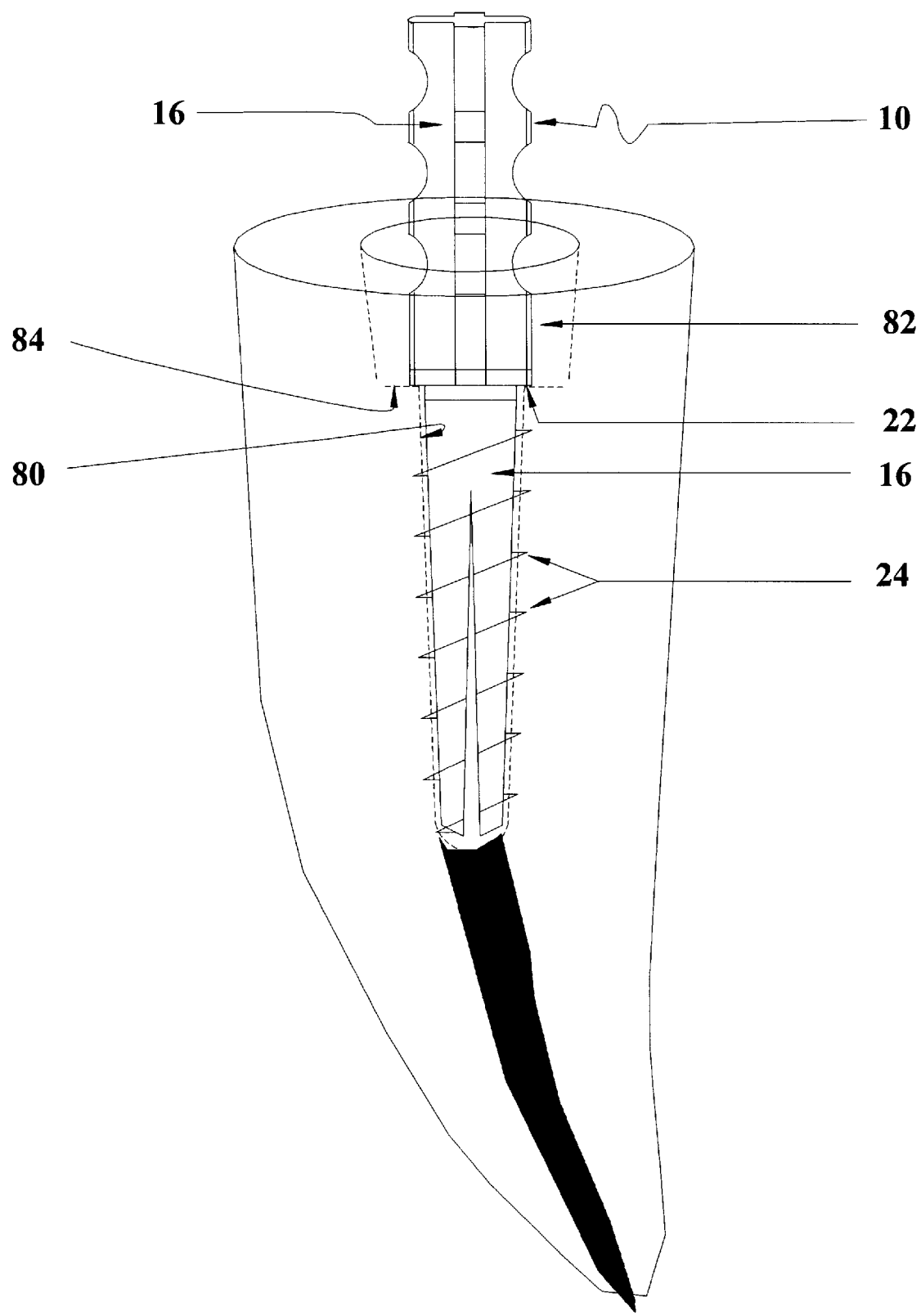
FIG. 5 illustrates a sagittal view of a tooth with the inner post inserted in the apical canal.

FIG. 5 illustrates the placement of the inner post 10 into the root-canal treated tooth. The threads 24 of the distal portion 16 engage the dentin of the apical canal 80 as the inner post 10 is screwed into the tooth. To increase the retention of the dental post and to take advantage of the split shank flexibility, the bore of the apical canal 80 is slightly smaller than the diameter of the distal portion 16 of the inner post 10. The inner post 10 is screwed into the tooth until the positive seat 22 engages the coronal ledge 84. The proximal portion 16 of the inner post 10 extends into the coronal canal 82. The distal portion 16 of the inner post 10 may optionally also be cemented in the apical canal 80 to increase retention.

Figure 6:
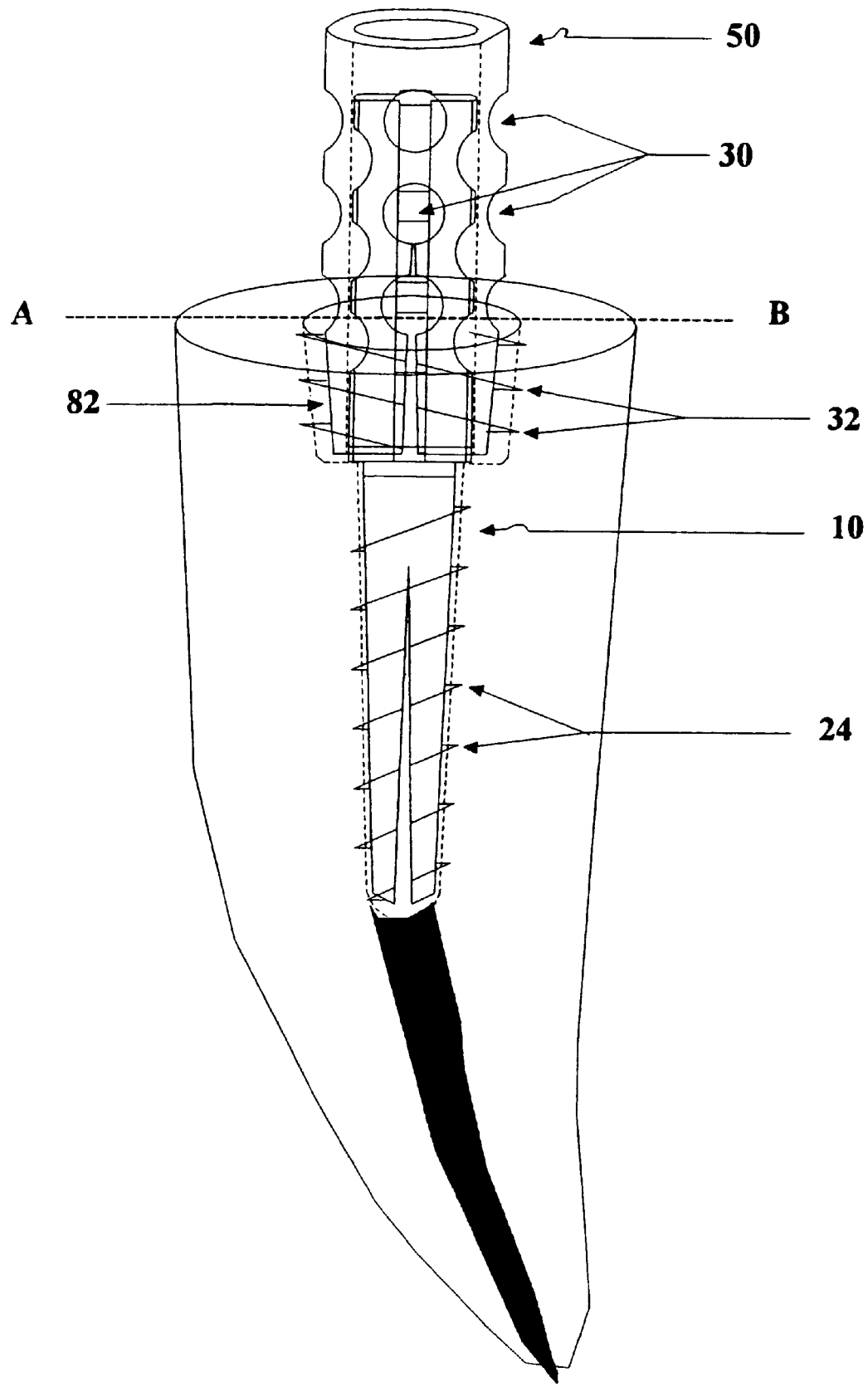
FIG. 6 illustrates a sagittal view of a tooth with both the inner post and outer sleeve inserted into the root canal.

FIG. 6 illustrates the placement of the outer sleeve 50 into the coronal canal 82 over the inner post 10. The threads 32 of the outer sleeve 50 engage the dentin of the coronal canal 82 as the outer sleeve 50 is screwed into the tooth. To increase the retention of the dental post and to account for the split shank flexibility, the bore of the coronal canal 82 is slightly smaller than the diameter of the outer sleeve 50. Once the outer sleeve 50 is in place, the outer sleeve 50 and the proximal portion 14 of the inner post 10 are bonded together either by dental cement or by a composite resin to make the core. The strength of the bond between the inner post 10 and outer sleeve 50 depends on the strength of the cement or resin and on good surface area contact, which is maximized by the holes 30 of the outer sleeve 50 and the perforations 74 of the inner post 10. Line A–B illustrates where the dental post could be sectioned by a dental drill to remove both the outer sleeve 50 and the inner post 10 from the tooth. By sectioning at A–B the majority of the bond between the outer sleeve 50 and the inner post 10 would be broken, allowing each component to be rotated individually. The outer sleeve 50 can then be unscrewed followed by a similar removal of the inner post 10.

Figure 7:
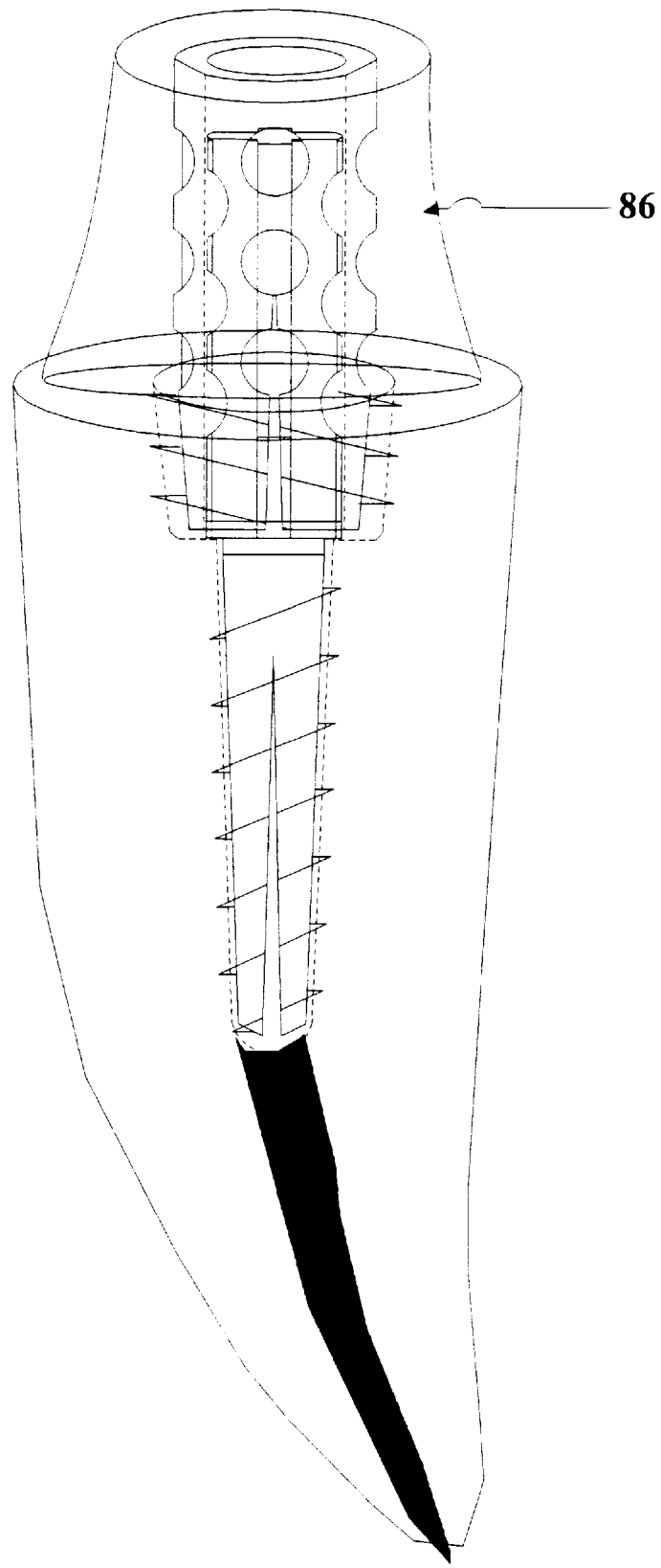
FIG. 7 illustrates a perspective view of a tooth both with the dental post of the present invention inserted into the root canal and with a core made of composite resin.

FIG. 7 illustrates a root-canal treated tooth with the dental post components in place and a core 86 build-up.

Figure 8:
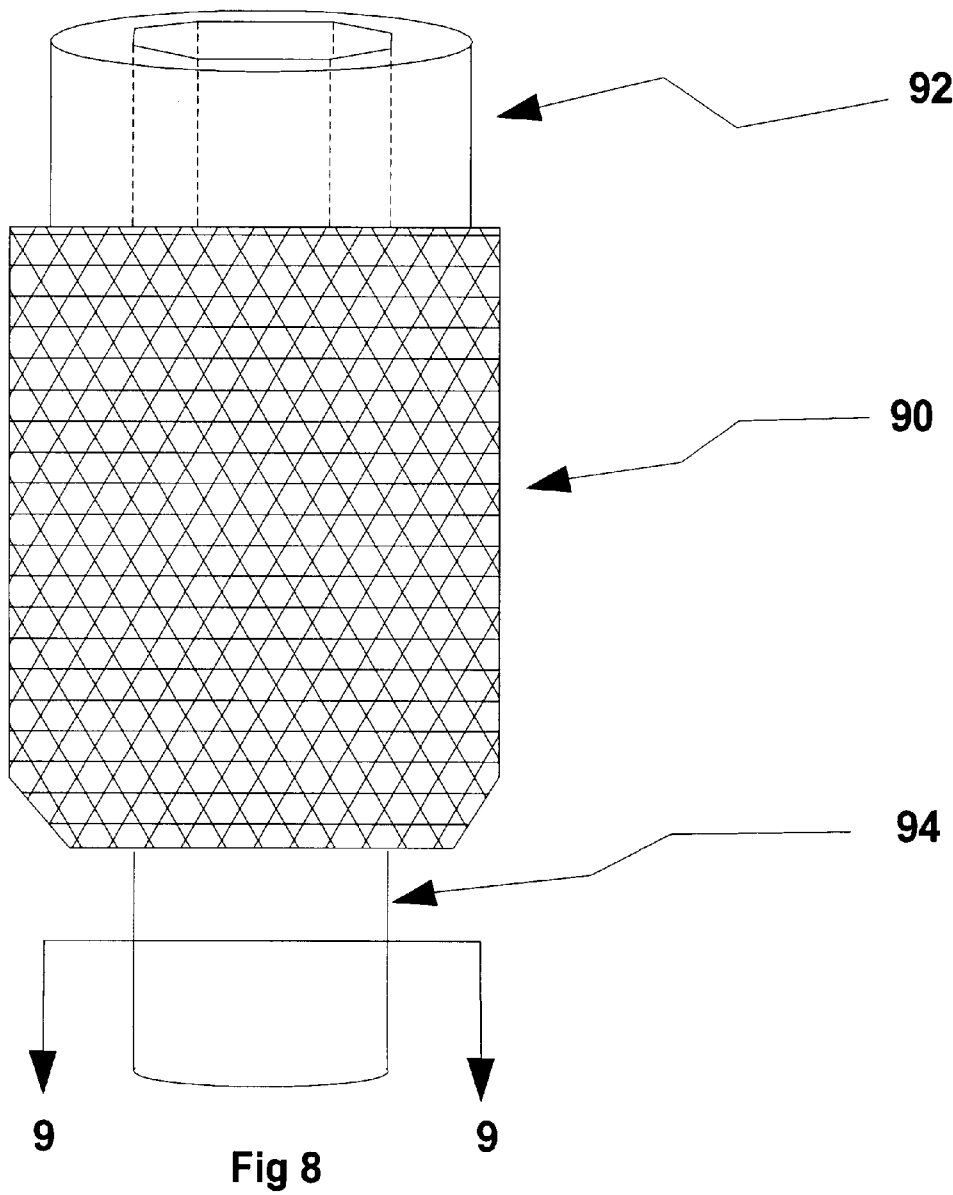
FIG. 8 illustrates a tool that could be used to insert into a tooth both the inner post and the outer sleeve.
Figure 9:
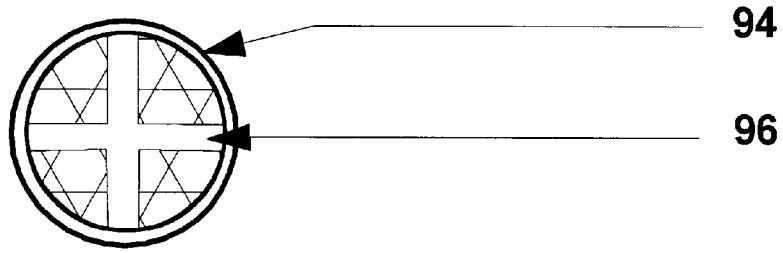
FIG. 9 illustrates a cross-section of the end of the tool used to insert the inner post into the tooth.

FIG. 8 illustrates a wrench tool 90 that could be used to insert the dental post components. The top portion 92 of different wrenches would be sized to fit the various diameters of the outer sleeve 50. The bottom portion 94 would be made to fit over the cross-bar shape of the proximal portion 14 of the inner post 10, as shown by the opening 96 in the cross-sectional view of the bottom portion 94 in FIG. 9.

The inner post and outer sleeve may be manufactured from any inert material that is suitable for dental applications, e.g., biologically compatible and resistant to attacks from body fluids. Preferred materials are surgical quality stainless steel and titanium alloys that are standard in the dental industry, with the most preferred being titanium alloys of aluminum and vanadium.

The shape and size of the proximal portion of the inner post can be varied so long as the outer sleeve is also adjusted to move over this proximal portion. Additionally, the proximal portion of the inner post and the outer sleeve could have compatible threads such that the outer sleeve would be threaded over the proximal portion of the inner post.

The lengths and diameters of the inner post and outer sleeve may be chosen to be useful when the tooth is drilled with standard dental drills. A possible range of diameters for the distal portion of the inner sleeve is between about 0.875 mm and about 1.9 mm. A possible range of outer diameters for the outer sleeve is between about 1.0 mm and about 2.5 mm. A possible range of lengths for the distal portion of the inner post is between about 8 mm and about 13 mm. A possible range of lengths for the proximal portion of the inner post is between about 3 mm and about 9 mm.

A possible range of lengths of the outer sleeve is between about 3 mmn and about 9 mm.

The term "dental cement" refers to any bonding agents suitable for dental applications, including zinc phosphate cements, glass ionomer cement, epoxy cements, and other cements or resins of use in bonding dental posts to tooth dentin.

The core material can be made of any common dental material. One example is a composite resin core, which has the advantage that it can also serve as a bonding agent between the proximal portion of the inner post and the outer sleeve.

The complete disclosures of all references cited in this specification are hereby incorporated by reference. In the event of an otherwise irreconcilable conflict, however, the present specification shall control.

I claim:

1. A two-component dental post comprising:
   (a) an inner post, comprising a distal portion which is threaded and a proximal portion;
   (b) an outer sleeve, comprising a channel adapted to move over the proximal portion of said inner post, a distal end, a proximal end, and threads on said distal end that are threaded in a direction opposite to the threads on said distal portion of said inner post;
   wherein said inner post is adapted to be screwed first into a tooth canal, said outer sleeve is adapted to be screwed second into a tooth, and said inner post and said outer sleeve are adapted to be cemented together, whereby said inner post and outer sleeve as screwed and cemented resist rotational forces.

2. A two-component dental post as in claim 1, wherein said distal portion of said inner post is tapered in a direction away from said proximortion of said inner post.

3. A two-component dental post as in claim 1, wherein said distal portion of said inner post contains a slot forming two legs.

4. A two-component dental post as in claim 1, wherein said distal portion of said inner post contains two slots forming four legs.

5. A two-component dental post as in claim 1, wherein the surface of at least one of said inner post and said outer sleeve is treated to enhance the cement bonding.

6. A two-component dental post as in claim 1, wherein the surface of said proximal portion of said inner post contains perforations.

7. A two-component dental post as in claim 1, wherein the surface of said outer sleeve contains holes.

8. A two-component dental post as in claim 1, wherein said outer sleeve and said proximal portion of the inner post have compatible threads such that said outer sleeve is threaded over said proximal portion of said inner post.

9. A two-component dental post as in claim 1, wherein the diameter of said distal portion of said inner post is between about 0.875 mm and about 1.5 mm.

10. A two-component dental post as in claim 1, wherein the outer diameter of said outer sleeve is between about 1.0 mm and about 2.5 mm.

11. A two-component dental post as in claim 1, wherein the length of said distal portion of said inner post is between about 8 mm and about 13 mm.

12. A two-component dental post as in claim 1, wherein the length of said proximal portion of said inner post is between about 3 mm and about 9 mm.

13. A two-component dental post as in claim 1, wherein the length of said outer sleeve is between about 3 mm and about 9 mm.

14. A method to secure a two-component dental post in a tooth, said method comprising the steps of:
    (a) providing a two-component dental post comprising an inner post, the inner post comprising a distal portion which is threaded and a proximal portion; and an outer sleeve, the outer sleeve comprising a channel adapted to move over the proximal portion of the inner post, a distal end, a proximal end, and threads on the distal end that are threaded in a direction opposite to the threads on the distal portion of the inner post;
    (b) drilling an apical canal in the dentin of the tooth such that the transverse dimension of the hole is smaller than the diameter of the inner post;
    (c) drilling a coronal canal in the dentin of the top of the tooth such that the transverse dimension of the hole is smaller than the diameter of the outer sleeve and larger than the diameter of the apical canal, wherein a coronal ledge is formed at the junction of the apical canal and the coronal canal;
    (d) screwing the inner post into the apical canal;
    (e) moving the outer sleeve over the inner post while simultaneously screwing the outer sleeve into the coronal canal until the outer sleeve touches the coronal ledge; and
    (f) introducing a dental cement between the proximal portion of the inner post and the outer sleeve and allowing the dental cement to cure;
    whereby said inner post and outer sleeve as screwed and cemented resist rotational forces.

15. A method as in claim 14, wherein the distal portion of the inner post is cemented to the apical canal.

16. A method as in claim 14, wherein the outer sleeve is cemented to the coronal canal.

* * * * *